United States Patent [19]

Laurin et al.

[11] 4,196,731
[45] Apr. 8, 1980

[54] SILICONE-CONTAINING THERMOPLASTIC POLYMERS FOR MEDICAL USES

[75] Inventors: Dean G. Laurin, Lake Zurich; Leonard F. Czuba, Lombard; Lawrence F. Becker, Chicago, all of Ill.

[73] Assignee: Baxter Travenol Laboratories, Inc., Deerfield, Ill.

[21] Appl. No.: 888,253

[22] Filed: Mar. 17, 1978

[51] Int. Cl.² .................... A61M 5/00; A61M 25/00
[52] U.S. Cl. .................... 128/214 R; 128/349 R; 128/348; 128/DIG. 21
[58] Field of Search .......... 128/214 R, 349, DIG. 21, 128/348; 260/827

[56] References Cited

U.S. PATENT DOCUMENTS

| | | | |
|---|---|---|---|
| 3,508,551 | 4/1970 | Walters et al. | 128/296 |
| 3,691,257 | 9/1972 | Kendrick et al. | 260/827 |
| 3,829,903 | 8/1974 | Stati et al. | 3/1 |
| 3,865,897 | 2/1975 | Falender | 260/827 |
| 3,932,555 | 1/1976 | Goodrich et al. | 260/827 |

FOREIGN PATENT DOCUMENTS 6715494  5/1968  Netherlands .................. 128/349 R

OTHER PUBLICATIONS

*Silicone Polyethylene Blends,* Polymer Engr. & Sci., vol. 16, No. 1, Jan. 1976, Falender.

*Primary Examiner*—Robert W. Michell
*Assistant Examiner*—Thomas J. Wallen
*Attorney, Agent, or Firm*—Paul C. Flattery; John P. Kirby, Jr.; Garrettson Ellis

[57] ABSTRACT

A flexible composition which is preferably radiopaque comprises a plastic material which may be mixed with from 10 to 50 percent by weight of a radiopaque filler. The plastic material comprises the product of (a) a block copolymer having thermoplastic, rubbery characteristics, having a central rubbery olefin block and terminal blocks of a polystyrene; (b) low crystallinity ethylene polymers such as poly (ethylene-vinyl acetate); and (c) a silicone gum containing a small amount of a silicon-bonded olefin group such as vinyl. Optionally, the addition of 5 to 40 percent by weight polypropylene may be included in these materials to improve their heat resistance and strength without affecting their transparency, when transparent materials are formulated.

23 Claims, 2 Drawing Figures

SILICONE-CONTAINING THERMOPLASTIC POLYMERS FOR MEDICAL USES

BACKGROUND OF THE INVENTION

Silicones, particularly polymers and copolymers of dimethylpolysiloxane, are used in numerous medical devices because of the known compatibility of the materials to living tissue. However, a drawback for the wider usage of silicone in the medical field is that it is expensive, and of relatively low tensile strength when compared with many other flexible plastic materials.

Accordingly, there is a need for stronger, less expensive materials than silicone; which at the same time exhibit equivalent tissue compatibility and non-clotting characteristics to silicone materials so that they may be used to make, for example, intravenous catheters designed for long-term retention in position of communcation with a blood vessel for the administration of parenteral solutions and the like.

Graft polymers including silicone materials are known, as described for example in U.S. Pat. No. 3,865,897. In this patent, graft polymers of silicone gums with polyethylene, polymethylpentene, polypropylene, and a copolymer of tetrafluorethylene repeating units and ethylene repeating units are disclosed, along with the teaching of how to graft them by placing them under shearing mixing conditions at elevated temperatures.

More details with respect to silicone-polyethylene blends are disclosed in the article entitled *Silicone Polyethylene Blends* by James R. Falender, et al in Polymer Engineering and Science, Vol. 16, No. 1, Jan., 1976. However, the materials of this type which have been tested have not exhibited satisfactory melt processability to get a smooth surface, or the desired higher ultimate strength and elastic behavior which would be desired for an intravenous catheter or a blood bag, for example.

Also, it is usually desired for intravenous catheters, in particular, to be radiopaque for purposes of visualization of the catheter on an X-ray fluoroscope or the like. However, silicone catheters which contain enough of a radiopaque filler such as barium sulfate to be strongly radiopaque may be of very low tensile strength. Polytetrafluoroethylene catheters and catheters made of many other materials which contain a high level of such a radiopaque filler, become unduly stiff.

Accordingly, there is a need for a flexible, plastic material which is relatively non-clotting and highly tissue compatible, and which can also remain flexible and strong at a high loading of radiopaque filler, for example on the order of 10 to 50 percent by weight.

The formulations of this invention exhibit good compatibility with tissue, reducing the normal irritation of tissue in the presence of a foreign material. Also they have low thrombogenicity, and thus can be used in longer-term contact with blood. Furthermore, the materials of this invention can remain relatively flexible and strong, when compared with other medical materials, even when loaded with extraordinarily high amounts of a radiopaque filler such as barium sulfate. Accordingly, tissue-compatible catheters for long-term implantation, and particularly, radiopaque catheters are advantageously made by this present invention.

DESCRIPTION OF THE INVENTION

In accordance with this invention, a flexible composition is provided, being made of a plastic material which comprises (a) from 30 to 50 percent by weight of a block copolymer having thermoplastic rubber characteristics and having a central block of a rubbery polyolefin, and terminal blocks of a polystyrene; (b) from 30 to 50 percent by weight of a thermoplastic low crystallinity ethylene polymer such as those selected from the group consisting of poly(ethylene-vinyl acetate) containing from 0 to 35 percent by weight of vinyl acetate units, or a low crystallinity polymer of ethylene containing from 0 to 60 percent by weight of propylene units, and having a molecular weight of at least about 10,000; and (c) from 2 to 30 percent by weight of a cross-linked silicone gum consisting of essentially of ($R_2SiO$) units, in which R is selected from the group consisting of methyl, phenyl, vinyl, and allyl, at least half of said R groups being methyl, and from 0.5 to 10 mole percent of said R groups being vinyl or allyl prior to crosslinking. The above percentages are calculated without regard to filler or other ingredients present apart from (a) and (b). Furthermore, we have discovered that the materials of this invention, when containing submicroscopic silica filler in conjunction with phenyl-containing silicones, are transparent at unexpectedly high levels of silicone and low levels of phenyl-group content.

The above-described materials have been found to be capable of accepting remarkably high loadings of radiopaque filler such as barium sulfate, for example, 10 to 50 percent by weight, while retaining adequate tissue compatibility, tensile strength, softness, and flexibility, unlike other known medical polymers. Accordingly, a tissue compatible, flexible catheter can be obtained which may be highly radiopaque, for example, I.V. catheters, central veinous catheters and Foley Catheters. The material may also be used for other medical uses such as blood or platelet bags, where a non-radiopaque material of this invention may be used. Particularly, a most desirable intravenous catheter may be made from the material of this invention, such as a central venous catheter capable of long-term emplacement for well in excess of a week without excessive blood clotting and tissue trauma.

It is generally preferred for about 20 to 40 percent of barium sulfate or other filler to be present as the radiopaque filler in the plastic material of this invention. However, other radiopaque fillers such as iodine-containing organic compounds, tungsten powder, or bismuth trioxide may also be used as partial or complete substitutes for the barium sulfate, in appropriate circumstances.

Ingredient (a), which is the block copolymer having thermoplastic rubber characteristics, is commercially available in various types and grades, for example, from the Shell Chemical Company under the trademark "KRATON," or from the Phillips Chemical Company under the trademark "SOLPRENE." The rubbery olefin central block may consist of such materials such polybutadiene, polyisoprene, or poly(ethylene-butylene), the latter being generally preferred. If desired, chain branching units and the like may also be included.

The rigid, usually terminal blocks of ingredient (a) customarily consist of polystyrene, although it is contemplated that derivatives of polystyrene and other equivalent materials can be used as well. Preferably, the Brookfield viscosity of ingredient (a) is 10 to 2000 cps., as a 10 weight percent toluene solution, measured at 25° C.

As ingredient (b), the poly(ethylene-vinyl acetate) preferably contains on the order of 25 to 30 percent by weight of vinyl acetate units, and is a thermoplastic polymer. Ingredient (b) serves as flow aid for extrusion of the material of this invention, and also serves to help provide a more flexible material, even in the presence of the high filler loadings contemplated in the preferred embodiments. The stiffness of the material of this invention can be controlled to some extent by adjusting the relative amounts of ingredients (a) and (b), ingredient (b) being of relatively low cost. Also, ingredient (b) can improve the grafting process of making these materials.

Ingredient (b) may also include generally low crystallinity polymers of principally ethylene, preferably having a molecular weight of at least 10,000, for example, low density polyethylene (e.g., a density of about 0.91 to 0.935 g/cc) and copolymers of ethylene containing up to 60 percent of co-polymerized propylene units, in which case the material is known as poly(ethylene-propylene).

Preferably, ingredients (a) and (b), along with any filler that is included, may be initially mixed, for example in a Brabender mixing chamber at a chamber temperature of approximately 190° C. The chamber is preferably flushed with nitrogen to eliminate oxygen.

Thereafter, ingredient (c), the silicone gum, may be added, and mixed with shearing action at a temperature typically of at least 190° C., although lower temperatures can be used with larger volume mixing equipment, on the order of 150 pounds of ingredients or the like, in which high shear stresses are obtained in the mixing chamber. Under these conditions, a crosslinking reaction is believed to take place in the silicone gum, to greatly reduce its migration from the final product plastic material. Also, a grafting reaction may take place under certain circumstances between the silicone gum and ingredients (a) or (b). These chemical reactions create a strengthened, flexible, elastomeric material having the desired characteristics specified above.

The silicone gum, ingredient (c), is preferably present in a concentration of about 5 to 20 percent by weight, without regard to filler or other ingredients than (a) and (b) present, for example, about 10 percent by weight. Typically, the silicone gum may have a molecular weight on the order of at least about 70,000 and preferably higher to render the silicone nonextractable from the completed material, and preferably contains a majority of dimethylsiloxane units so that R as defined above is predominantly methyl. However, as an alternative, phenylmethylsiloxane and diphenylsiloxane units may also be included, along with other equivalent siloxane units that do not significantly change the properties of the material, when and as desired. Branched chain siloxane gums may also be used.

As stated above, in the silicone gum, from essentially 0.5 to 10 mole percent of the R groups should be vinyl or allyl, preferably 3 to 6 mole percent, with vinyl groups being localized in blocks or clusters in the molecule, in order to impart more completely the desirable properties of silicone to the completed material. These are preferably provided in the form of vinylmethylsiloxane units, although vinyl-containing siloxane units such as divinyl siloxane, allylmethylsiloxane, or trivinyl siloxane units may also be used in equivalent quantities.

Alternatively, silicone-bonded reactive groups can be used in combination with or as a substitute for alkenyl groups. For example, silicone gums with Si-H units can crosslink with silicon-bonded vinyl-containing gums, especially in the presence of platinum catalysts. The various other well-known crosslinking systems for silicone gums may also be used in appropriate circumstances, such as silicones with attached groups of acetoxy, hydroxy, ethoxy, methoxy and acryloxypropyl siloxane.

The silicone gum provides a surprising degree of softness and flexibility to the finished product, especially at high filler loadings. Surprisingly, silicone gum generally, when mixed in small amounts such as 5 to 30 weight percent with other organic polymers of higher tensile strength, provides a softer material capable of accepting larger amounts of fillers, and particularly barium sulfate, than the silicon-free organic polymers.

Preferably, 40 to 50 percent by weight each of ingredients (a) and (b) may be present in the pure plastic material of this invention, while from 8 to 15 percent by weight of ingredient (c) may be present, without regard to filler or other ingredients than (a) and (b) present.

While not wishing to be restricted to any theory of operation of the synthesis of the formulation of this invention, it is believed that the vinyl or allyl groups on the silicone molecular participate in a crosslinking or grafting process to provide the finished product claimed in this invention.

Other materials may be added to the formulation of this invention as desired. For example, a reinforcing type submicroscopic silica filler may be utilized, especially when silane-treated for compatibility with the polymer. However, it has been generally found that increased amounts of ingredient (c), the silicone gum, are needed in this circumstance because of the strong affinity of silane-treated reinforcing silica filler for the silicone gum. The incorporation of submicroscopic silica into transparent embodiments of the invention of this application permits the addition of larger amounts of silicones, and silicones at lower refractive index, while retaining transparency.

Other materials such as antioxidants, pigments, and the like may be added as well, but the formulation of this invention is preferably free of leachable liquid components such as oil plasticizers.

Heat resistance, strength, and stiffness may be increased by adding 5 to 40 percent by weight of highly crystalline polyolefins, such as polypropylene, polymethylpentene, polyethylene and copolymers of such, without necessarily diminishing the transparency of those compositions which are transparent without this addition.

Particularly, when highly crystalline polyolefins are used, it is generally preferred to use from 5 to 25 percent by weight of such a material, for example, polypropylene, the percentage being based on the entire weight of the composition.

When submicroscopic or fume silica is used, it is generally preferred for approximately for 10 to 30 percent by weight to be present, based upon the weight of the entire composition.

It has been particularly found that when clear compositions in accordance with this invention are desired to be used, the use of phenyl-containing silicone compositions tend to improve the clarity. It has been found that when fume silica is used as a filler, equal clarity in a composition can be achieved while using a silicone composition having a lower phenyl content, which is generally a less expensive material.

Figure 1:
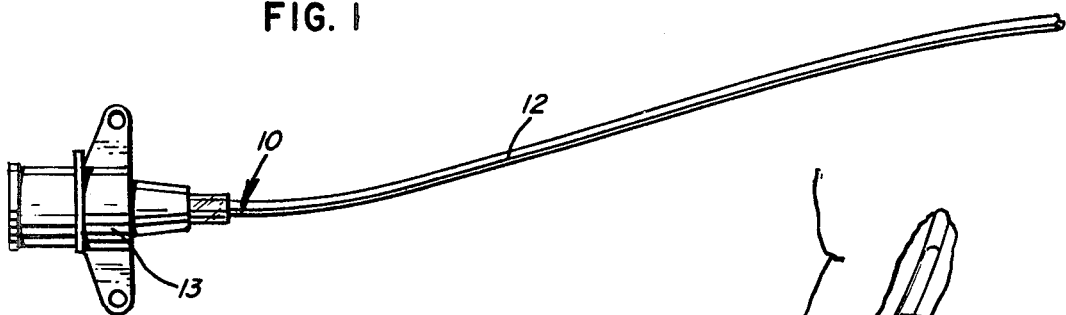
FIG. 1 is a perspective view of a central veinous catheter made in accordance with this invention.

Referring to the drawings, the central veinous catheter 10 comprises a flexible, tubular shaft 12 which may be made of the elastomeric material of this invention, and a conventional hub 13 at one end thereof, which may be made of any desired plastic material. Hub 13 is provided as a connector member for other parts, and may also be used as a suturing site to prevent withdrawing of the catheters, as is conventionally known.

Figure 2:
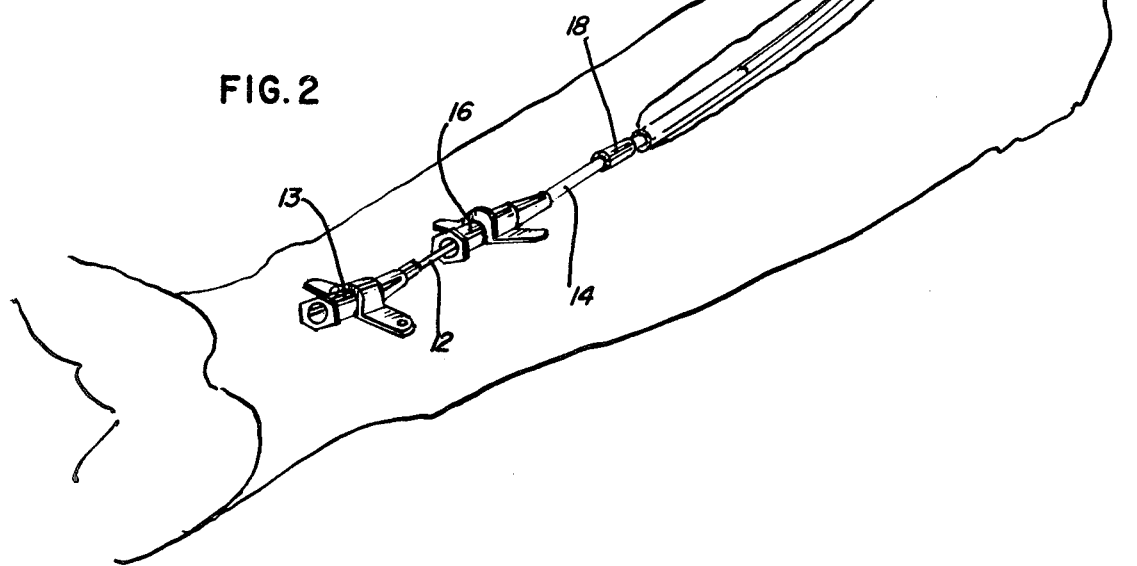
FIG. 2 is a perspective view of the central veinous catheter of this invention shown emplaced in a patient.

As shown in FIG. 2, the catheter of this invention may be inserted into a vein of a patient by being passed through a relatively short introducer catheter 14 which, in turn, carries at its end a hub 16. A connection from a parenteral solution source or the like may then communicate through the bore of hub 16 to provide fluid connection through hub 13 and catheter 12.

The above catheter system may be similar to the CENTRASIL TM silicone elastomer central veinous catheter which is currently sold by the Vicra Division of Travenol Laboratories, Inc., Dallas, Texas, with the material of catheter shaft 12 being made in accordance with this invention for good flexibility, softness, kink resistance, thrombo-resistance, high strength, and low friction, in conjunction with good visibility by X-ray.

Catheter guard 18 is placed near the front end of introducer catheter 14 after the emplacement of central veinous catheter 12, with the introducer catheter 14 being withdrawn out of the central vein, but its tip is still allowed to remain in subcutaneous position in the final emplacement. This reduces the possibility of irritation to the vein.

The examples below are provided for illustrative purposes only, and are not intended to limit the scope of the invention of this application, which is as defined in the claims below.

EXAMPLE 1

To a Brabender Plasticorder, Model MV100, with an attached mixing/measuring head, purged with nitrogen gas and heated to 195° C., was added (a) 13.5 grams of a block copolymer (KRATON G1662) having thermoplastic rubber characteristics, with a central block of ethylene and butylene copolymer units in generally equal molar proportions, and terminal blocks of polystyrene, in which the ethylene-butylene portion of the copolymer comprises about 70 percent by weight of the copolymer molecule, and the material has a Brookfield viscosity at 25° C. of 20 cps., using a 10 weight percent solution in toluene, and containing from 0.03 to 0.07 percent by weight of A0330 antioxidant (sold by Ethyl Corporation); (b) 13.5 grams of poly(ethylene-vinyl acetate) having a vinyl acetate content of 28 percent and a melt index of 3.5, as tested by ASTM test D-1238-73, condition E, (Ultrathene UE 634-00, sold by U.S. Industries); and 12.8 grams of finely powdered barium sulfate (Blanc Fixe XR [Barium Sulfate XR] sold by the Ore and Chemical Co.).

This mixture was mixed in the Brabender device for two minutes under a nitrogen atmosphere. Following this, 3.0 grams of (c) a dimethylpolysiloxane gum containing approximately 5 weight percent of methylvinylsiloxane units (Union Carbide Y8203 or Rhodia Co. RC356) was added. The Brabender fixed cam blade rotor type mixing chamber was brought to a final temperature of 225° C. while exerting maximum torque in the shearing mixing. The reaction time to maximum torque was 2.7 minutes, followed by a mixing time of 3.3 minutes. The initial torque was 2150 meter·grams, and the final torque 2245 meter·grams. The final temperature of the material processed was 238° C. with the Brabender mixing rotors rotating at 190 r.p.m.

The above process was repeated on fifteen separate occasions to provide sufficient material for extrusion of a tube. Thereafter, a tube having a bore diameter of approximately 0.035 inch and an outer diameter of 0.065 inch was extruded out of the material. The extruded tubing was cut into 21 inch lengths, and hubs were attached to the tubing as illustrated in the drawing and described above, for providing central veinous catheters.

The resulting central veinous catheters exhibit excellent tissue compatibility, as illustrated by superior non-thrombogenic characteristics of the type generally exhibited by silicone rubber. The catheters were flexible and highly radiopaque, while retaining improved tensile strength, lower friction, and were easier to maintain free of attracted dust and the like, compared with pure silicone catheters having similar or lesser amounts of barium sulfate or tungsten as a filler.

EXAMPLE 2

To the previous Brabender mixing device, purged with nitrogen gas, and heated to 195° C. was added (a) 40 parts by weight of a block copolymer (KRATON G1650) having thermoplastic rubber characteristics with a central block of ethylene and butylene copolymer units in equal molar portions, and terminal blocks of polystyrene, the material having a Brookfield viscosity of 1,500 cps. at 20 weight percent in toluene at 77° F.; 40 parts by weight of (b) a poly(ethylene-vinyl acetate) thermoplastic having 28 percent by weight of vinyl acetate units and a melt index of 1.5 (Union Carbide DQDA2803). These materials were mixed in the Brabender mixing chamber in pelletized form under nitrogen at 140 r.p.m. No filler was used.

Thereafter, 20 parts by weight of (c) a soft silicone gum (General Electric 449-336-15) having a viscosity of 55 million centipoises at 25° C,. and containing 4 mole percent vinylmethylsiloxane units, 20 mole percent diphenylsiloxane units, and essentially the balance being dimethylsiloxane units, were added to provide a 40 gram batch in the compounding machine. The machine was operated for four minutes under nitrogen at 140 r.p.m. in a mixing and purge cycle, and thereafter for four minutes for completion of the grafting process. The initial torque was 1720 meter·grams, and a final torque of 2480 meter·grams. The initial oil temperature of the compounding machine was 208° C. and the final temperature of the material was 239° C.

Thereafter, the material was allowed to cool for 1½ minutes under nitrogen at 20 r.p.m., removed and extruded as tubing which was strong, soft, kink-resistant, heat sealable, having good thromboresistant characteristics and imroved transparency for viewing blood.

The refractive index of the silicone material is selected to essentially match the refractive index of the other ingredients for improved clarity.

Addition of 10 weight percent polypropylene (Rexene 23M2, made by Rexene Polyolefins Co.) having a melt flow rate of 2.0 and a density of 0.895 g/cc provides a transparent material also capable of steam sterilization. It has high gas permeability, which is advantageous for storing blood components, especially platelets.

EXAMPLE 3

The formulation of Example 1 was prepared; enough barium sulfate radiopaque filler was added to provide a formulation in which the amount of barium sulfate present was 40 percent by weight of the amount of plastic material. The resulting product still exhibited acceptable flexibility, kink-resistance, strength, and thromboresistance, although showing slightly more trauma to the inside blood vessel wall.

EXAMPLE 6

The process of Example 2 was repeated, utilizing 45 percent by weight of the KRATON G1650 material for ingredient (a); 45 percent of the same ethylene vinyl acetate copolymer for ingredient (b), and using no filler. After initial mixing under a nitrogen purge in the Brabender blending device, 10 percent by weight of Union Carbide W980 silicone gum was added, being a random copolymer gum of dimethylsiloxane units and 3.5 weight percent methylvinylsiloxane units, and end blocked with trimethylsiloxane units.

The mixture was fluxed at 140 r.p.m. under nitrogen for 1.6 minutes at an oil temperature of 217° C. in the Brabender blending device. Then the silicone was added with the temperature of the mixture being read at 223° C. initially, and an initial torque of 2010 meter-grams. After processing at 140 r.p.m. for 1.5 minutes, the torque had risen to 2230 meter·grams. The final temperature of the mixer was 234° C. and resulted in an extrudable mixture capable of forming catheters and other medical devices which had good thromboresistant characteristics and good tensile strength.

EXAMPLE 5

To the Brabender Plasticorder of Example 1, purged with nitrogen gas and heated to 195° C. was added 49 parts by weight of the KRATON G1650 block copolymer described in Example 2; 21 parts by weight of a poly(ethylene-propylene copolymer containing 60 to 70 weight percent of ethylene units (EXXON Vistalon 702).

This mixture was mixed in the Brabender device at 60 r.p.m. until mixed, after which 30 parts by weight of a dimethylpolysiloxane gum containing 2.9 percent by weight of a vinylmethylsiloxane units (Union Carbide W980) was added. The rotation of the Brabender device was then increased to 160 r.p.m. with a jacket temperature of 217° C. After reaction the final material temperature was 236° C. and the final torque was 1980 meter·grams.

The resulting product was molded into a sheet which was strong, flexible, and non-greasy, indicating the crosslinking of the silicone in the formulation.

EXAMPLE 6

To the Brabender Plasticorder mixing chamber of Example 1, using techniques similar to Example 1, was added 24.45 grams of a blend of KRATON G1650, Vistalon 701 and DQDA2803 (see below) in such proportion as to achieve the final weight percent composition below. Then 15.56 grams of a diphenyl dimethylpolysiloxane with added vinyl groups (G.E. 449-358-52) with silane-treated fumed silica (Degussa, Inc. Aerosil R-972) in such proportions as to achieve the composition described below was added. These ingredients were then mixed under a nitrogen cover at high shear stress to final conditions of 230° C. at 140 r.p.m. There was immediately added polypropylene, i.e., Rexene 23M2, which contains a few weight percent ethylene and has a melt flow rate of 2.0 grams/10 minutes at 230° C. according to ASTM method D1238-73 and has a density of 0.895 g/cc at 73° F. The final weight percent composition was 35.8 percent KRATON; 9.6 percent Vistalon 701; 9.6 percent DQDA2803, 10 percent Rexene 23M2; 15% Aerosil R-972 and 20 percent phenyl methylvinylsiloxane. See Example 2 for descriptions of KRATON G1650 and DQDA2803.

Vistalon 701 is an ethylene-propylene copolymer made by EXXON Chemical Co. to contain approximately 67 weight percent ethylene and 33 weight percent of propylene units, having a Mooney viscosity of 75 (260° C., 1+8 minutes) and a fairly narrow molecular weight distribution.

Aerosil R972 is a fumed silica whose surface is treated with dimethyldichlorosilane, and is made to have an average primary particle size of 16 nm., a surface area of 130 square meters per gram (BET method), and a refractive index of 1.45.

The phenylmethylvinyl silicone was 449-358-52 was made by General Electric Company to have approximately 18 million centipoise viscosity (25° C.), refractive index 1.5095 ($n_D$ at 22° C.), having 20 mole percent diphenylsiloxane units and 3 mole percent vinylmethylsiloxane units.

The above material was compression molded to make a sheet approximately 15 mils thick, which was transparent, flexible, resilient, and had a higher yield strength and less tackiness, compared to similar materials without silica. The sheet was fabricated by impulse heat sealing to make a water filled bag, which withstood steam sterilizing without becoming sticky or distorting, and without permenent change in clarity. (Haziness that developed during steam sterilization cleared out completely in one day at room conditions. This hazing, commonly called "blush," is typical of many other materials, especially those materials used to contain drugs and human blood or blood fractions.) This material is permeable to carbon dioxide at a rate of 102–123 cc-cm/cm-sec-mmHg$\times 10^{10}$, which is approximately three to four times higher than currently commercial vinyl blood and blood-platelet containers.

That which is claimed is:

1. A flexible, radiopaque composition which comprises a plastic material mixed with from 10 to 50 percent by weight of a radiopaque filler, said plastic material comprising the product of (a) 30 to 50 percent by weight of a block copolymer having thermoplastic rubber characteristics and having a central block of a rubbery polyolefin and terminal blocks of a polystyrene; (b) from 30 to 50 percent by weight of a thermoplastic material selected from the group consisting of poly(ethylene-vinyl acetate) containing up to 35 percent by weight of vinyl acetate units and low-crystallinity polymers of ethylene containing from 0 to 60 percent by weight of propylene units, and having a molecular weight of at least about 10,000; and (c) from 2 to 30 percent by weight of a chemically reactive crosslinkable or graftable silicone gum consisting essentially of ($R_2SiO$) units, in which R is selected from the group consisting of methyl, phenyl, allyl, and vinyl, at least half of said R groups being methyl, and no more than 10 mole percent of said R groups being allyl and vinyl.

2. The composition of claim 1 in which said radiopaque filler is barium sulfate.

3. The composition of claim 1 in which said rubbery olefin is a copolymer of generally equal proportions of ethylene and butylene units.

4. The composition of claim 1 in which some 40 to 50 percent by weight of each of ingredients (a) and (b) are present and from 5 to 20 percent by weight of ingredients (c) is present, said percentages being based on the composition without filler and other additives.

5. The flexible composition of claim 1 in which said siloxane units are free of phenyl groups.

6. The flexible, radiopaque composition which is formed when the chemically reactive silicone gum is cross-linked or grafted in the composition of claim 1.

7. The flexible radiopaque composition of claim 1 in which ingredient (b) is a low-crystallinity polymer of ethylene containing 30 to 40 weight percent of propylene units.

8. The flexible radiopaque composition of claim 1 in which ingredient (b) contains at least ten percent by weight of vinyl acetate units.

9. The elastomer of claim 1 which is essentially free of leachable liquid components.

10. A flexible composition made of a plastic material which comprises (a) from 30 to 50 percent by weight of a block copolymer having thermoplastic rubber characteristics and having a central block of a rubbery polyolefin and terminal blocks of a polystyrene; (b) from 30 to 50 percent by weight of a poly(ethylene-vinyl acetate) containing from 10 to 35 percent by weight of vinyl acetate units; and (c) from 2 to 30 percent by weight of a chemically reactive grafted silicone gum consisting of essentially of ($R_2SiO$) units, in which R is selected from the group consisting of methyl, phenyl, and vinyl, at least half of said R groups being methyl, and from 0.5 to 10 mole percent of said R groups being vinyl, prior to their chemical reaction.

11. The elastomer of claim 10 which is essentially free of leachable liquid components.

12. A catheter comprising a flexible tubular shaft and a hub affixed on one end thereof, said catheter shaft being made of a flexible, radiopaque composition which comprises a plastic material mixed with from 10 to 50 percent by weight of a radiopaque filler, said plastic material comprising the grafted product of (a) 30 to 50 percent by weight of a block copolymer having thermoplastic rubber characteristics and having a central block of a rubbery polyolefin and terminal blocks of a polystyrene; (b) from 30 to 50 percent by weight of a thermoplastic material selected from the group consisting of poly(ethylene-vinyl acetate) containing from 10 to 35 percent by weight of vinyl acetate units and low-crystallinity polymer of ethylene containing from 0 to 60 percent by weight of propylene units, and having a molecular weight of at least about 10,000; and (c) from 2 to 30 percent by weight of a crosslinked or grafted silicone gum consisting of essentially of ($R_2SiO$) units, in which R is selected from the group consisting of methyl, phenyl, allyl and vinyl, at least half of said R groups being methyl.

13. The catheter of claim 12 which is an intravenous catheter.

14. The catheter of claim 12 in which said radiopaque filler is barium sulfate.

15. The catheter of claim 14 in which said rubbery olefin is a copolymer of generally equal proportions of ethylene and butylene units.

16. The catheter of claim 15 in which some 40 to 50 percent by weight each of ingredients (a) and (b) are present and from 5 to 20 percent of ingredient (c) is present, said percentages being based on the composition without filler and other additives.

17. The catheter of claim 16 in which said siloxane units are free of phenyl.

18. The elastomer of claim 12 which is essentially free of leachable liquid components.

19. A flexible composition which comprises a plastic material, said plastic material comprising the product of (a) 30 to 50 percent by weight of a block copolymer having thermoplastic rubber characteristics and having a central block of a rubbery polyolefin and terminal blocks of a polystyrene; (b) from 30 to 50 percent by weight of a thermoplastic material selected from the group consisting of poly(ethylene-vinyl acetate) containing from 10 to 35 percent by weight of vinyl acetate units and low crystallinity polymers of ethylene containing from 0 to 60 percent by weight of propylene units and having a molecular weight of at least about 10,000, (c) from 2 to 30 percent by weight of a chemically reactive, crosslinkable, or graftable silicone gum consisting essentially of ($R_2SiO$) units, in which R is selected from the group consisting of methyl, phenyl, allyl and vinyl, at least half of said R groups being methyl, and no more than 10 percent of said R groups being allyl and vinyl; and (d) from 5 to 40 percent by weight of a highly crystalline polyolefin for improved heat-resistant strength and stiffness.

20. The composition of claim 19 in which said highly crystalline polyolefin is polypropylene which is present in the amount of 5 to 25 percent by weight.

21. The composition of claim 19 in which from 10 to 30 percent by weight of submicroscopic silica is present, based on the weight of the entire composition.

22. The composition of claim 21 in which, in said crosslinkable silicone gum which is present, at least 10 mole percent of said R groups are phenyl.

23. A flexible composition which comprises a plastic material mixed with a filler, said plastic material comprising the product of (a) 30 to 50 percent by weight of a block copolymer having thermoplastic rubber characteristics and having a central block of a rubbery polyolefin and terminal blocks of a polystyrene; (b) from 30 to 50 percent by weight of a thermoplastic material selected from the group consisting of poly(ethylene-vinyl acetate) containing from 10 to 35 percent by weight of vinyl acetate units and low crystallinity polymers of ethylene containing from 0 to 60 percent by weight of propylene units, and having a molecular weight of at least about 10,000; (c) from 2 to 30 percent by weight of a chemically reactive crosslinkable or graftable silicone gum consisting essentially of ($R_2SiO$) units, in which R is selected from the group consisting of methyl, phenyl, allyl and vinyl, at least half of said R groups being methyl, and no more than 10 mole percent of said R groups being allyl and vinyl, and at least 10 mole percent of said R groups being phenyl; said filler being submicroscopic silica and being mixed with said plastic material in the amount of 10 to 30 percent by weight of said plastic material.

* * * * *